United States Patent
Van Alstine et al.

(10) Patent No.: US 8,093,373 B2
(45) Date of Patent: Jan. 10, 2012

(54) PLASMID PURIFICATION

(75) Inventors: James Van Alstine, Uppsala (SE); Jan Bergström, Uppsala (SE); Dag Lindström, Vattholma (SE); Joachim Stadler, Freiburg (DE)

(73) Assignee: GE Healthcare Bio-Sciences AB, Uppsala (SE)

( * ) Notice: Subject to any disclaimer, the term of this patent is extended or adjusted under 35 U.S.C. 154(b) by 1313 days.

(21) Appl. No.: 10/589,740

(22) PCT Filed: Feb. 21, 2005

(86) PCT No.: PCT/SE2005/000229
§ 371 (c)(1),
(2), (4) Date: Aug. 16, 2006

(87) PCT Pub. No.: WO2005/083080
PCT Pub. Date: Sep. 9, 2005

(65) Prior Publication Data
US 2007/0161000 A1 Jul. 12, 2007

(30) Foreign Application Priority Data
Feb. 26, 2004 (SE) .................................. 0400490

(51) Int. Cl.
*C07H 21/00* (2006.01)

(52) U.S. Cl. .................... 536/25.4; 536/23.1; 435/320.1

(58) Field of Classification Search ........................ None
See application file for complete search history.

(56) References Cited

U.S. PATENT DOCUMENTS

| | | |
|---|---|---|
| 6,011,148 A | 1/2000 | Bussey et al. |
| 6,214,586 B1 | 4/2001 | McNeilly |
| 6,242,220 B1 | 6/2001 | Wahle et al. |
| 6,270,970 B1 | 8/2001 | Smith et al. |
| 6,313,285 B1 | 11/2001 | Butler et al. |
| 6,441,160 B2 | 8/2002 | Kitamura et al. |
| 6,498,236 B1 | 12/2002 | Lihme et al. |
| 6,572,766 B1 | 6/2003 | Bergstrom et al. |
| 6,602,990 B1 | 8/2003 | Berg |
| 7,026,468 B2 * | 4/2006 | Nochumson et al. ........ 536/25.4 |
| 2001/0014650 A1 | 8/2001 | Smith et al. |
| 2002/0001812 A1 | 1/2002 | Smith et al. |
| 2003/0171443 A1 | 9/2003 | Erbacher |

FOREIGN PATENT DOCUMENTS

| | | |
|---|---|---|
| WO | WO 99/63076 | 12/1999 |
| WO | WO 01/37987 | 5/2001 |

OTHER PUBLICATIONS

Arshady, R., "Styrene Based Polymer Supports Developed by Suspension Polymerization", *La Chimica e L'Industria*, vol. 70, No. 9, 1988, p. 70-75.

Hjerten, S., "The Preparation of Agarose Spheres for Chromatography of Molecules and Particles", *Biochim. Biophys. Acta*, vol. 79, No. 2, 1964, p. 393-398.

\* cited by examiner

*Primary Examiner* — Jim Ketter

(57) ABSTRACT

The present invention relates to a method of isolating at least one plasmid from other components of a liquid, which method comprises the steps of providing a separation matrix comprised of one or more porous carriers, which carrier(s) present anion exchange groups on external surfaces as well as pore surfaces and a pore size distribution that does not allow access of plasmids to pore surfaces; contacting said matrix with the liquid to allow adsorption of the plasmids to ligands present on the separation matrix; contacting an eluent with the separation matrix to release the plasmids and recovering plasmids from a fraction of said eluent. Thus, the present method allows the plasmids to adsorb to the external surfaces of the matrix, while other components such as RNA is adsorbed onto the pore surfaces. In one embodiment, the matrix presents a DNA exclusion limit of at least about 270 base pairs; such as at least about 1,000 base pairs.

9 Claims, 5 Drawing Sheets

PLASMID PURIFICATION

CROSS REFERENCE TO RELATED APPLICATIONS

This application is a filing under 35 U.S.C. §371 and claims priority to international patent application number PCT/SE2005/000229 filed Feb. 21, 2005, published on Sep. 9, 2005, as WO 2005/083080, which claims priority to application number 0400490-9 filed in Sweden on Feb. 26, 2004; the disclosures of which are incorporated herein by reference in their entireties.

TECHNICAL FIELD

The present invention relates to the field of biotechnology, and more specifically to the purification of nucleic acids, especially plasmids. More specifically, the present invention relates to a method of liquid chromatography, wherein plasmids are isolated from other components of a liquid, such as a cell lysate. The invention also embraces a kit that enables purification of plasmids using the present method.

BACKGROUND OF THE INVENTION

The industrial application of biotechnology is based on the more recent advances within the field of molecular biology and genetics. As is well known, one of the ways that genetic variability is maintained within a population is through recombination, a process involving the exchange of genetic information among different DNA molecules that results in a reshuffling of genes. To provide recombination in the field of genetic engineering, a vector is usually used. The most commonly used vector is the DNA plasmid, a small genetic element that permits microorganisms to store genetic information elsewhere than in the nucleus.

Thus, plasmids have become useful elements in many biotechnological applications these days. For example, to produce recombinant proteins, genetic engineering of cells is performed by introducing plasmids that carry a gene encoding a protein, which is not expressed in the native cell. Thereby, many proteins useful primarily in the medical and diagnostic fields are easily produced using methods that have become more or less routine methods.

Another use of plasmids as vectors is in the field of gene therapy, which is expected to be one of the fastest growing areas in the next decade. Gene therapy is a therapeutic strategy where nucleic acids are introduced into human cells in order to cure genetic defects e.g. cystic fibrosis. The first human gene therapy trials began in 1990, using an ex vivo strategy. In this approach, the patient cells are harvested and cultivated in the laboratory and then incubated with vectors, such as plasmids, to introduce the therapeutic genes. Even though alternative approaches for delivering genes based on in vivo gene therapy, wherein a viral vector is directly administered to the patient, have been suggested more recently, the plasmid is expected to retain its importance in gene therapy. Thus, the increased use of such applications results in a need for large quantities of plasmid DNA. To this end, an efficient large-scale purification process, which can meet specifications in purity and quantitation, is required.

Conventionally, the production of plasmid DNA involves fermentation, primary purification and high-resolution separation.

Thus, firstly, the fermentation step commonly comprises to produce the plasmid DNA in bacteria, such as *Escherichia coli*, and will also involve a step for release of plasmid DNA from the bacterial cells known as lysis. In general, cell lysis can be achieved by a variety of chemical or mechanical methods, such as by addition of alkali or using a French press, respectively. However, for reasons of safety and to not harm the product, the alkaline lysis will be preferred in the production of plasmid DNA. Usually, several contaminants such as RNA, genomic DNA, proteins, cells and cells debris are released in such an alkaline lysis step.

Secondly, with regard to the primary purification step, methods such as two-phase systems, e.g. using polyethylene glycol (PEG) and a salt; temperature-induced phase separation using a thermoseparating polymer that separates into two phases at a to certain temperature; or size exclusion chromatography, sometimes denoted gel filtration, are commonly used.

With regard to the high-resolution separation step, chromatography is a commonly used technique. As is well known, the term chromatography embraces a family of closely related separation methods, which are all based on the principle that two mutually immiscible phases are brought into contact. More specifically, the target compound is introduced into a mobile phase, which is contacted with a stationary phase. The target compound will then undergo a series of interactions between the stationary and mobile phases as it is being carried through the system by the mobile phase. The interactions exploit differences in the physical or chemical properties of the components in the sample. The basis for the chromatographic principle known as ion exchange process is the competitive binding of ions of one kind, such as proteins or nucleic acids, for ions of another kind, such as salt ions, to an oppositely charged matrix known as the ion exchanger. The interaction between the target compound and the ion exchanger depends on several factors, such as net charge and surface charge distribution of the target compound, the ionic strength and the nature of the particular ions in the solvent, the proton activity (pH) etc.

Anion exchange chromatography has been suggested for purification of nucleic acids and plasmids. For example, WO 99/63076 (The Immune Response Corp.) discloses large scale plasmid purification using a single, "mixed mode" anion exchange step. The method disclosed requires a stringent ethanol wash to remove endotoxins and other impurities. More specifically, by increasing the amount of organic solvent in the wash step, the disclosed method shifts from a purely ionic mode to that of a "mixed" mode. The separation matrix used is e.g. triethylaminoethyl (TMAE) fractogel anion exchange resin (E.M. Science Fractogel TMAE Resin).

U.S. Pat. No. 6,270,970 (Smith et al) relates to mixed-bed solid phases for isolation of target nucleic acids, which are comprised of at least two different solid phases. Both phases bind the target nucleic acids, but under different solution conditions, and they release the nucleic acid under similar elution conditions. The solid phase of the different beds preferably comprise magnetic silica particles, and at least one preferably has an ion-exchange residue capable of exchanging with the target nucleic acid covalently attached to the surface of the support material. The term "surface" is stated to refer to the portion of the support material of a solid phase which comes into direct contact with a solution when the solid phase is combined therewith. Thus, the anion exchange ligands are present on external surfaces as well as on pore surfaces, as is evidenced by the statement that suitable anion-exchanger solid phases for use in the mixed-bed solid phases according to U.S. Pat. No. 6,270,970 are commercially available, illustrated e.g. by Sepharose™. The pore size of such commercial solid phases is commonly in a range that allows plasmids and similar size molecules to enter their interior.

Further, U.S. Pat. No. 6,441,160 (Tosoh Corp.) discloses plasmid purification using hydrophobic interaction chromatography (HIC), optionally combined with an anion exchange step. In the HIC step, protein and RNA are adsorbed at a salt concentration at which plasmids are not adsorbed to produce an eluate comprising plasmid and DNA. Thus, the liquid applied to the anion exchange column should not contain any RNA. A general disadvantage of using HIC is the requirement of high salt concentrations at the start, which due to crystallisation and precipitation are relatively difficult to handle. Suitable anion exchange separation matrices are stated to have a particle diameter of 2-500 µm and an average pore diameter of 1500-4000 Å. An illustrative anion exchange separation matrix is DEAE 5PW (Tosoh). However, U.S. Pat. No. 6,441,160 teaches that plasmid purification from a cleared lysate by means of anion exchange interaction chromatography alone is not advantageous, as evidenced by comparative Example 1 wherein it is concluded that many impurities were contained in the plasmid fraction obtained from a single anion exchange step. In said comparative example, a chromatography column having an inner diameter of 7.5 mm and a length of 7.5 cm was used.

U.S. Pat. No. 6,011,148 (Megabios Corp.) discloses a method for purification of nucleic acids, such as plasmid DNA, by circulating a plasmid containing solution through an ultrafiltration unit under conditions sufficient to allow a gel layer to form and filtering the solution through the ultrafiltration unit to provide a permeate solution and a retentate solution, whereby the nucleic acid is retained in the retentate solution. The filtration device used should have open channels, to avoid shear and decrease of yield of retained nucleic acid. An advantage of the method is that it avoids use of toxic chemicals and organic solvents, such as phenol, chloroform, ether etc, which may cause safety and regulatory concerns. Another advantage of the method is the high purity of the product obtained. The method can optionally be combined with a step of anion exchange for further purification, particularly from contaminating endotoxin, trace proteins, and residual cellular contaminants.

U.S. Pat. No. 6,214,586 (Genzyme Corp.) discloses a method for purifying plasmid DNA from a mixture containing plasmid DNA and genomic DNA comprising to treat a solution containing both plasmid DNA and genomic DNA with at least 80% by weight saturation with ammonium sulphate, thereby precipitating the genomic DNA and providing purified plasmid DNA in solution. The method may be combined with a step of reverse phase and anion exchange chromatography, in which case a preferred resin is Poros 50 DE2, a column of which is equilibrated preferably with a solution of 50 mM acetate, pH 5.4, 1 mM EDTA, 0.5 M NaCl, and 9.5% ethanol.

U.S. Pat. No. 6,313,285 (Genentech Inc.) discloses a process for purifying plasmid DNA from prokaryotic cells, wherein there is no use of enzymes to digest RNA. More specifically, the process comprises the steps of: (a) digesting the cells; (b) incubating the cells in the presence of alkali and a detergent to effect lysis and solubilisation thereof; (c) removing lysate contaminants to provide a plasmid DNA solution; (d) filtering the solution through a tangential flow filtration device to obtain a retentate containing the plasmid DNA; and (e) collecting the retentate. The process may comprise a subsequent step of anion exchange chromatography.

U.S. Pat. No. 6,242,220 (Qiagen GmbH) discloses an improved protocol for separation of ccc DNA from genomic DNA, which protocol not only provides ccc DNA of a high purity grade but also removes proteinaceous impurities. More specifically, the suggested method comprises to precipitate a cleared lysate with alcohol; to wash the precipitate with an alcohol solution; to resuspend the precipitate; to digest the resuspended precipitate with a RecBCD nuclease (EC 3.1.11.5); and to separate purified ccc DNA from the remainder of the product obtained by contacting it with an ion exchange material. RNAse may be added to the cleared lysate, and the precipitation step is stated to separate the DNA of the cells from other components, including RNA and proteins.

U.S. Pat. No. 6,498,236 (Upfront Chromatography A/S) relates to a method for the isolation of immunoglobulins from a solution, which method allows high efficiency and use of little or no salts, especially lyotropic salts. Solid phase matrices are used, preferably epichlorohydrin activated agarose matrices, which have been functionalised with aromatic or heteroaromatic ligands which preferably comprises an acidic substituent such as a carboxylic acid, i.e. a weak cation exchange group. Alternatively, the matrix backbones are dextran-based, such as Sephadex™, cellulose-based, such as Perloza™ cellulose, composite beads, such as Sephacryl™ and Superdex™, synthetic origin beads such as Fractogel™ etc.

Further, U.S. Pat. No. 6,572,766 (Amersham Biosciences) discloses a separation matrix comprising a core showing a micropore system and a surface in which the pore system has openings, wherein the surface is covered with a polymer which exhibits such a large molecular weight that it cannot penetrate into the micropore system. Thus, the polymer has a molecular weight distribution of such a kind that all or substantially all polymer molecules in the preparation are excluded from transport into the micropores, when the preparation is contacted with a liquid which can be transported into the matrix. The polymer may be functionalised with a different ligand from the micropore surfaces. This means that the polymer, when it is anchored to the outer surface, can give separation characteristics to the surface, which are different from the separation characteristics of the micropores. The method is suggested for separation of nucleic acid, proteins including peptides and other organic and inorganic compounds.

Finally, WO 01/37987 (Amersham Biosciences) relates to the separation of negatively charged nucleic acids from each other and from other negatively charged components such as proteins. More specifically, disclosed is a the use of an adsorbent that exhibits an interior part, which carries a ligand structure capable of binding to substances I and II, and is accessible to substance I, and an outer surface layer which is free from ligand structures and which is more easily penetrated by substance I than by substance II. Thus, since there are no ligands present on the outer surface layer, i.e. the external surface, adsorption will be limited to the interior part, i.e. the pore surfaces. The outer surface may even carry repelling structures. Thus, substance I will be adsorbed within the adsorbent, while structure II will pass through the column without being adsorbed. Substance I and/or II may exhibit a nucleic acid structure. The process is e.g. useful for separating linear DNA from circular DNA, RNA from plasmids, plasmids from genomic DNA, plasmids from endotoxins etc. The process is optionally followed by further steps. For example, if substance II is desired in a highly purified form, it should be followed by an additional capture step, such as ion exchange, revered phase chromatography (RPC), HIC etc.

However, there is still a need in this field of alternative purification schemes enabling isolation of large target compounds, such as plasmids, at high productivity and selectivity.

BRIEF SUMMARY OF THE INVENTION

Thus, one aspect of the present invention is a large scale method of selective capture of high molecular weight nucleic acids, such as plasmids. This can be achieved as described in the appended claims.

Another aspect of the present invention is a method of plasmid purification, which method provides an increased productivity.

Another aspect of the invention is a method of plasmid purification, which avoids precipitation steps and to which no additions of enzymes and/or detergents are required.

Another aspect of the present invention is a method of plasmid purification, which method utilises a non-fouling and autoclavable separation matrix.

The aspects above can be achieved as described in the appended claims. Further aspects and advantages of the present invention will appear from the detailed description that follows.

DEFINITIONS

Figure 1:
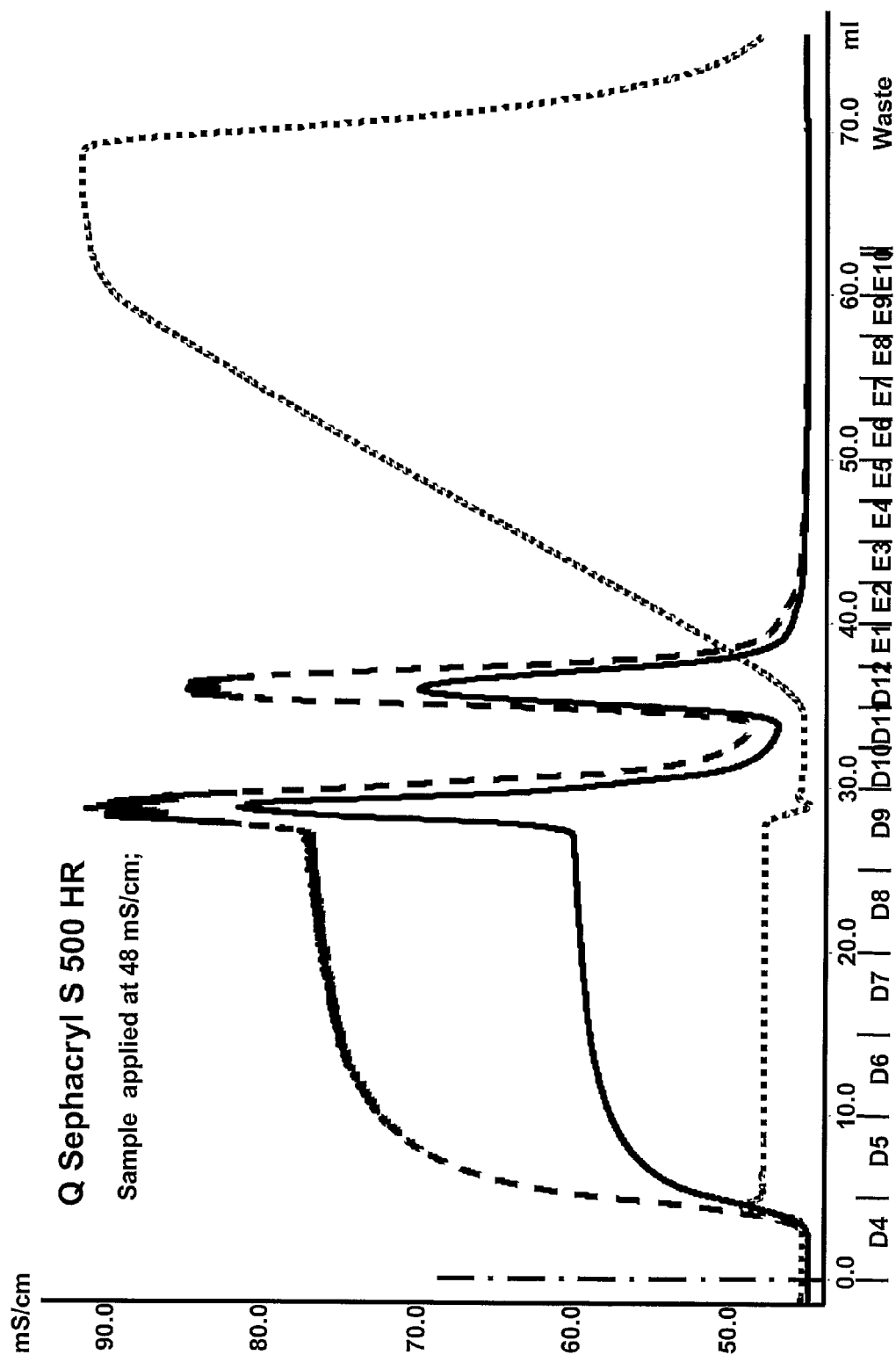
FIG. 1 shows a chromatogram illustrating isolation of plasmids according to the invention on a separation matrix based on allyl dextran and N,N'-methylenebisacrylamide to which quaternary anion exchange groups have been coupled.

The term "plasmid" is used herein interchangeably with the term "plasmid DNA" and encompasses the various plasmid forms i.e. open circular (oc), also known as nicked plasmid DNA and supercoiled (ccc) plasmid DNA.

The term "anion exchange groups" means groups that are positively charged or chargeable.

The term "nucleic acid molecules" is used herein synonymously with the term "nucleotides" and includes DNA, e.g. plasmids and other DNA, such as genomic DNA, as well as RNA, such as mRNA, tRNA and sRNA.

The term "clarified lysate" is also well known in the art and refers to an aqueous solution containing plasmid DNA, RNA and proteins which is obtained after alkaline lysis of cultured cells or unicellular organisms in the presence of SDS and the separation of the cell debris, usually by filtration or centrifugation, followed by potassium acetate precipitation of the protein-SDS complex (micelles).

The term a "separation matrix" refers to a material which is useful as the stationary phase in chromatography. Commonly used chromatographic separation matrices are comprised of a carrier to which functional groups have been coupled.

The "surface" of a separation matrix as used herein includes both the external surface of the matrix and the pore surfaces. The "external surface" means the outside, and hence includes the external pore openings, as opposed to the term "pore surfaces", which is used herein for the pore surfaces that appear in the interior.

The term "functional groups" means in the context of liquid chromatography groups capable of sufficient interaction to impart separation of different compounds. Such interaction may be adsorption or retardation.

The term "purification" means herein isolation of a desired component from other components.

The term "capture" refers to the initial step of a separation procedure. Most commonly, a capture step includes clarification, concentration, stabilisation and a significant purification from soluble contaminants. After the capture step, an intermediate purification may follow, which removes most of the significant impurities including RNA, genomic DNA, oc DNA, viruses and endotoxins. The final purification step is commonly referred to a "polishing", and removes trace contaminants and impurities to leave an active, safe product. Contaminants removed during the polishing step are often conformers of the target molecule or suspected leakage products.

The terms "size exclusion" and "gel filtration" are used herein interchangeably and means separation of compounds based on their molecular size in a sieving effect.

The term a "separation matrix" means a support to which ligands comprising functional groups have been coupled.

The term "$D_{50}$ value" means in the context of particle diameters the volume median of a particle distribution.

DETAILED DESCRIPTION OF THE INVENTION

The present invention relates to a method of isolating at least one plasmid from other component(s) of a liquid, which method comprises the steps of a) providing a separation matrix comprised of one or more porous carriers, which carrier(s) present anion exchange groups on external surfaces as well as on pore surfaces and a pore size distribution that does not allow access of plasmids to the pore surfaces;

b) contacting said matrix with the liquid to adsorb the plasmid(s) to ligands present on the external surfaces of the separation matrix; and, optionally, c) contacting an eluent with the separation matrix to release the plasmid(s) and recovering plasmid(s) from a fraction of said eluent.

Thus, due to the pore size of the carrier, the plasmids will be sterically hindered from being adsorbed to its interior. The present invention is distinguished from the above-discussed WO 01/37987 in that in the present method, plasmids are adsorbed to the external surfaces of the porous carriers that constitute the separation matrix, while in WO 01/37987; plasmids are merely sieved through the matrix and not adsorbed to the neutral external surface of the adsorbent disclosed therein. In the present context, it is understood that the phrase "does not allow access of plasmids" means that substantially no plasmids can enter the pore system.

Accordingly, the present invention relates to a method of isolating at least one plasmid from other component(s) of a liquid, which method comprises the steps of a) providing a separation matrix comprised of one or more porous carriers, which carrier(s) present anion exchange groups on external surfaces as well as pore surfaces;

b) contacting said matrix with the liquid to provide plasmid adsorption limited to the ligands present on the external surfaces of the separation matrix; and, optionally, c) contacting an eluent with the separation matrix to release the plasmid(s) and recovering plasmid(s) from a fraction of said eluent.

In the present context, it is understood that the phrase "limited to the ligands present on the external surfaces of the separation matrix" means that substantially no plasmid adsorption takes place to the pore surfaces, i.e. the interior of the carrier.

In one aspect, the present invention relates to a method of isolating at least one plasmid from other component(s) of a liquid, which method comprises the steps of a) providing a separation matrix comprised of one or more porous carriers, which carrier(s) present anion exchange groups on external surfaces as well as pore surfaces and a DNA exclusion limit of at least about 270 base pairs;

b) contacting said matrix with the liquid to adsorb the plasmid(s) to ligands present on the external surfaces of the porous separation matrix; and, optionally, c) contacting an eluent with the separation matrix to release the plasmid(s) and recovering plasmid(s) from a fraction of said eluent.

In a specific embodiment, the DNA exclusion limit of the porous separation matrix is at least about 800, or at least about 1,000, such as 1,000-10,000 bp. In another embodiment, the DNA exclusion limit of the porous separation matrix is about 20,000 bp. Thus, the DNA exclusion limit of the porous separation matrix may be within intervals of 800-30,000 bp, such as 1,000-20,000 bp. As the skilled person in this field will realise, the sizes of target plasmids and the DNA exclusion limit of the porous separation matrix may be varied in relation to each other in order to obtain a separation according to the invention.

The plasmid will commonly originate from a fermentation procedure. The fermented cells may be eukaryotic or prokaryotic, preferably prokaryotic, such as bacteria, e.g. *E. coli* or *B. subtilis*. In an alternative embodiment, the cells that produces the plasmids to be purified are yeast species, such as *saccharomyces, piccia* etc. Strains producing the desired plasmid are prepared in accordance with standard methods of molecular biology, or obtained from commercial sources. The lysis can for example be performed by adding cells to alkaline buffers, such as 0.2 NaOH/1.5% SDS, as is well known in the art. Addition of potassium acetate may be used to precipitate impurities, such as chromosomal DNA, RNA and cellular proteins. Following lysis and neutralisation, the lysate may be collected and clarified, for example by ultrafiltration through a suitable filter having a pore diameter of about 0.1-100 μm. In an advantageous embodiment, the lysate is then concentrated using techniques well known in the art, such as ultrafiltration, preferably by using hollow fibre membranes. In addition, the resulting liquid may be adjusted by water in order to reduce ionic strength to obtain the desired properties before its contact with the separation matrix as defined in step (b), where adsorption of the plasmids may be achieved based on net charge. The liquid applied to the present separation matrix will usually be of a viscosity in a range that would have necessitated certain precautions in the prior art methods, such as a limited flow rate. However, the invention allows relatively high flow rates, while maintaining the rigidity of the beads. Commonly, the present method will utilise flow rates above about 100 cm/h. Consequently, the present method enables to allow a high degree of recovery as compared to prior art methods for plasmid purification, which is especially advantageous in large scale preparation.

Thus, in one embodiment, the present method is a large scale method, wherein at least about 1 grams of plasmid is recovered. Large scale preparation is commonly performed in chromatography columns, the diameter of which is at least about 10 cm. For example, for large scale preparation, a bed height of 15 cm, which would require an amount of about 1.2 liters of separation matrix, may be used. However, as the skilled person in this field will realise, larger amounts of matrix are also useful for large scale preparation, also known as preparative scale. Such a method is especially advantageous for preparation of plasmids for therapeutic applications, which plasmids are relatively large as compared to the plasmids conventionally used as vectors in recombinant DNA techniques. Consequently, in one embodiment, the size of the plasmids isolated in accordance with the present invention is from about 3,000 base pairs, such as about 5,000 or 6,000 base pairs, and may be up to about 10,000 base pairs.

The present method allows separating plasmids from one or more other components, such as contaminants, in a liquid. In the most advantageous embodiment of the present invention, the method is a capture step wherein the plasmids are separated from RNA. In a specific embodiment, the RNA is adsorbed to ligands present on the pore surfaces of the separation matrix. In one embodiment of the present invention, plasmids are adsorbed solely, i.e. exclusively, to the external to surface of the separation matrix. In an alternative embodiment, the DNA exclusion limit of the matrix is selected so that the plasmids are adsorbed to the pore surfaces as well. In a specific embodiment, the separation matrix is selected so that the plasmids are adsorbed to the surfaces and to the pore surfaces adjacent to the external surfaces, such as in the close proximity of the external surfaces, but not as far within the separation matrix as the RNA. In this embodiment, the plasmids are adsorbed within an external layer of the carrier.

In one embodiment, the present method also comprises a step (d), wherein the plasmid-containing eluate resulting from step (c) is subject to hydrophobic interaction chromatography (HIC). Such a HIC step can be carried out on any kind of conventional HIC matrix in accordance with well known principles of adsorption and elution. The HIC step is advantageous since it will remove endotoxins, and it can also be utilised to separate open circular plasmids (oc) from closed circular plasmids (ccc). An advantageous feature of running HIC subsequent to anion exchange is that HIC adsorption commonly takes place at high conductivities. More specifically, the plasmids are commonly eluted from the ion exchanger by addition of salt, and the HIC step can advantageously be carried out at such salt concentrations, or higher, without any requirement of volume demanding dilutions. Further, in the most advantageous embodiment of the present invention, the anion exchange step is preceded by a filtration.

As mentioned above, the present separation matrix is comprised of a carrier to which ligands have been coupled. Said carrier is advantageously of a particle size and porosity in the range commonly known for size exclusion media. Thus, the present separation media may be defined as a size exclusion media, to which positively charged or chargeable anion exchange groups have been immobilised.

Further, the separation matrix used in the present method may be in any suitable form, such as essentially spherical particles; a monolith; or a membrane. In the most advantageous embodiment, the matrix is in the form of particles having an average particle diameter in a dry state of about 10-60 μm, such as about 10-50 μm. In a specific embodiment, the average particle diameter is about 30-50 μm. In order to keep the backpressure low and consequently to allow use of low pressure equipment, the particle size distribution of the separation matrix should be kept as homogenous as possible. In this context, "low pressure" means a pressure below about 3 bars. Further, the particle diameters given herein refer to $D_{50}$ values.

The ion-exchange groups immobilised to the carrier may be any well-known charged or chargeable groups, known as weak and strong anion exchangers, respectively. As the skilled person in this field will realise, the density or substitution degree of the anion-exchange groups can be varied. However, it is noted that too high densities may be disadvantageous, as it may result in unnecessarily strong adsorption and a consequent loss in selectivity.

Examples of anion exchange groups suitable for the present separation matrix are mono-, di- and trialkylamines, such as trimethylamine (Q), dimethylamine, diethylamine (ANX), and tert-butylamine; hydroxyl-containing amines, such as ethanolamine, di- and triethanolamine, and trishydroxymethylaminometan (TRIS); mixed alkyl and hydroxyl-containing amines, such as hydroxyethyl amine, hydroxymethyldimethylaminometan and N-ethyl-N-hydroxyethylamine; amines containing aromatic groups, such as aniline, dimethylaniline, and hydroxyethylaniline; amines with combinations of aromatic, aliphatic and hydroxyl-containing groups; ligands with aminofunctions combined with acidic functions, such as carboxyl, sulphonate and phosphate groups, provided they have a positive net charge, such as arginine and lysine; pyridine; morpholine, piperazine, pyrrazine, guanidine, and amines containing several nitrogen atoms.

In one embodiment, said anion exchange groups are selected from the group that consists of quaternary amine (Q) groups and diethylamine groups. Such groups are well known (see e.g. Protein Purification—Principles, High Resolution Methods and Applications, Janson and Rydén 1989 VCH Publishers, Inc.). In a specific embodiment, the groups are bimodal or multimodal groups comprising at least one further functional group in addition to the ion exchange group.

The carrier may be inorganic or organic, and may comprise a coating such as a hydroxyl-containing layer attached to the carrier surfaces.

In one embodiment, the carrier is a synthetic polymer, preferably a cross-linked synthetic polymer, such as styrene or styrene derivatives, divinylbenzene, acrylamides, acrylate esters, methacrylate esters, vinyl esters, vinyl amides, vinyl ethers etc. Such polymers are easily produced according to standard methods (see e.g. "Styrene based polymer supports developed by suspension polymerization" (R Arshady: Chimica e L'Industria 70(9), 70-75 (1988))).

In an alternative embodiment, the carrier is a cross-linked carbohydrate material, such as agarose, agar, cellulose, dextran, chitosan, konjac, carrageenan, gellan, and alginate. In one embodiment, the matrix is porous cross-linked agarose. Such a carbohydrate carrier is easily prepared by the skilled person in this field in accordance with standard methods, such as inverse suspension gelation (S Hjertén: Biochim Biophys Acta 79(2), 393-398 (1964)). To obtain an improved rigidity of the matrix, the matrix may be prepared as described in U.S. Pat. No. 6,602,990 (Berg et al).

In yet an alternative embodiment, the carrier is an inorganic material, such as silica.

Alternatively, the separation matrix can be made by functionalisation of a commercially available product for size exclusion, such as Sephacryl™ (available from Amersham Biosciences, Uppsala, Sweden). Such a commercial product can easily be modified by the skilled person in this field with ligands that comprises functional groups (for an overview, see e.g. Immobilised Affinity Ligand Techniques, Hermanson, Mallia and Smith, 1992 by Academic Press, Inc.). Thus, in a specific embodiment, the carrier is made from allyl dextran cross-linked with bisacrylamide. In an illustrative embodiment, the carrier is Sephacryl™ S-500 HR or Sephacryl™ S-1000 SF (Amersham Biosciences).

In an advantageous embodiment, the present method is performed in a chromatography column packed using standard methods with the matrix, and the liquid is passed over said matrix by any conventional means, such as by gravity or use of pumping devices. The optimal flow rate and contact time for step (b) will depend e.g. on the kind of ion exchange groups and the nature of the carrier. The skilled person in this field can easily adjust the suitable conditions and buffers for each case using common general knowledge or by reference to the standard textbooks in the field. Further, one or more conventional washing steps may be included, if appropriate. The elution of step (c) may comprise a stepwise or linear gradient, and again the skilled person in this field can easily select suitable conditions and buffers using common general knowledge or standard textbooks in the field.

In a second aspect, the present invention relates to the use of a separation matrix comprised of one or more porous carriers, which carrier(s) present anion exchange groups on external surfaces as well as pore surfaces and a pore size distribution that does not allow access of plasmids to pore surfaces, for the purification of plasmids. In one embodiment, the invention relates to the use of a porous separation matrix comprised of a carrier to the surfaces of which anion exchange groups have been immobilised, which matrix presents a DNA exclusion limit of at least about 270 base pairs, for the purification of plasmids. In one embodiment, said separation matrix is used as a capture media in liquid chromatography to isolate plasmids from contaminants such as RNA and endotoxins. In an advantageous embodiment of the present use, the plasmids isolated i.e. purified comprise covalently closed circular (ccc) DNA. In this embodiment, the ccc plasmids are separated from other plasmid isoforms, as well as from the above-discussed contaminants. Plasmid DNA is used to an increasing extent within the therapeutic field, such as in the manufacture of vectors for gene therapy. Thus, in one embodiment, plasmid DNA is isolated for use in personalised medicine, to provide a drug designed for the treatment of a specific individual. Other uses of the plasmids isolated according to the present invention are for example for research purposes and in the diagnostic field.

The separation matrix used according to this aspect may be any one of the above described, and the details regarding to the method may apply to the present use. The reason for using the DNA exclusion limit rather than a pore size to define the present separation matrix is that most of the herein disclosed carriers are gels, i.e. in a wet state. The standard method for determination of pore sizes is by mercury porosimetry, which however requires a dry sample. As a porous gel dries, its pore structure will change and eventually collapse. Accordingly, when pore sizes are defined for porous gels, they have commonly been estimated indirectly by packing a column with a size exclusion gel, running an experiment and noting retention data for model compounds of known molecular weight. However, the pore distribution of a porous gel may still present a large variety of pore sizes, and consequently the $K_{av}$ or $K_D$ for defined molecules and the DNA exclusion limit should be a more reliable way of defining the porosity of a gel. These terms are well known within this field and are used herein with their conventional meaning.

In an advantageous embodiment, the separation matrix is in the form of essentially spherical particles having an average particle diameter of 10-60 μm, such as 10-50 μm, e.g. 30-50 μm.

The present use may include purification of plasmids in large scale, such as in amounts of about 1 gram or more.

In a third aspect, the present invention relates to a kit comprising, in separate compartments, a separation matrix comprised of one or more porous carriers, which carrier(s) present anion exchange groups on external surfaces as well as pore surfaces and a pore size distribution that does not allow access of plasmids to pore surfaces; at least one buffer; and written instructions that describes how plasmids are purified from other components of a liquid using said kit. In one embodiment, the invention is a kit comprising, in separate compartments a separation matrix comprised of a carrier to the surfaces of which anion exchange groups have been immobilised, which matrix is porous and presents a DNA exclusion limit of at least about 270 base pairs; at least one buffer; and written instructions for the purification of plasmids from other components of a liquid. The separation matrix of the kit may be in the form of essentially spherical particles; a monolith; a membrane or the like, and may be further defined as described above. In an advantageous embodiment, the matrix is in the form of essentially spherical particles packed in a chromatography column. The column may be made from any conventional material, such as a biocompatible plastic, e.g. polypropylene, or glass. The column is preferably of a size suitable for large-scale purification of plasmids, preferably having a diameter of 10 cm or more. In a specific embodiment, the column according to the invention is provided with luer adaptors, tubing connectors, and domed nuts.

DETAILED DESCRIPTION OF THE DRAWINGS

FIG. 1 shows a chromatogram illustrating isolation of plasmids according to the invention on a separation matrix based on allyl dextran and N,N'-methylenebisacrylamide to which quaternary anion exchange groups have been coupled, namely Q-Sephacryl™ 500 prepared as described in example 1 below. The conductivity used was 48 mS/cm, and the separation matrix presents a DNA exclusion limit of about 1,078 base pairs.

Figure 2:
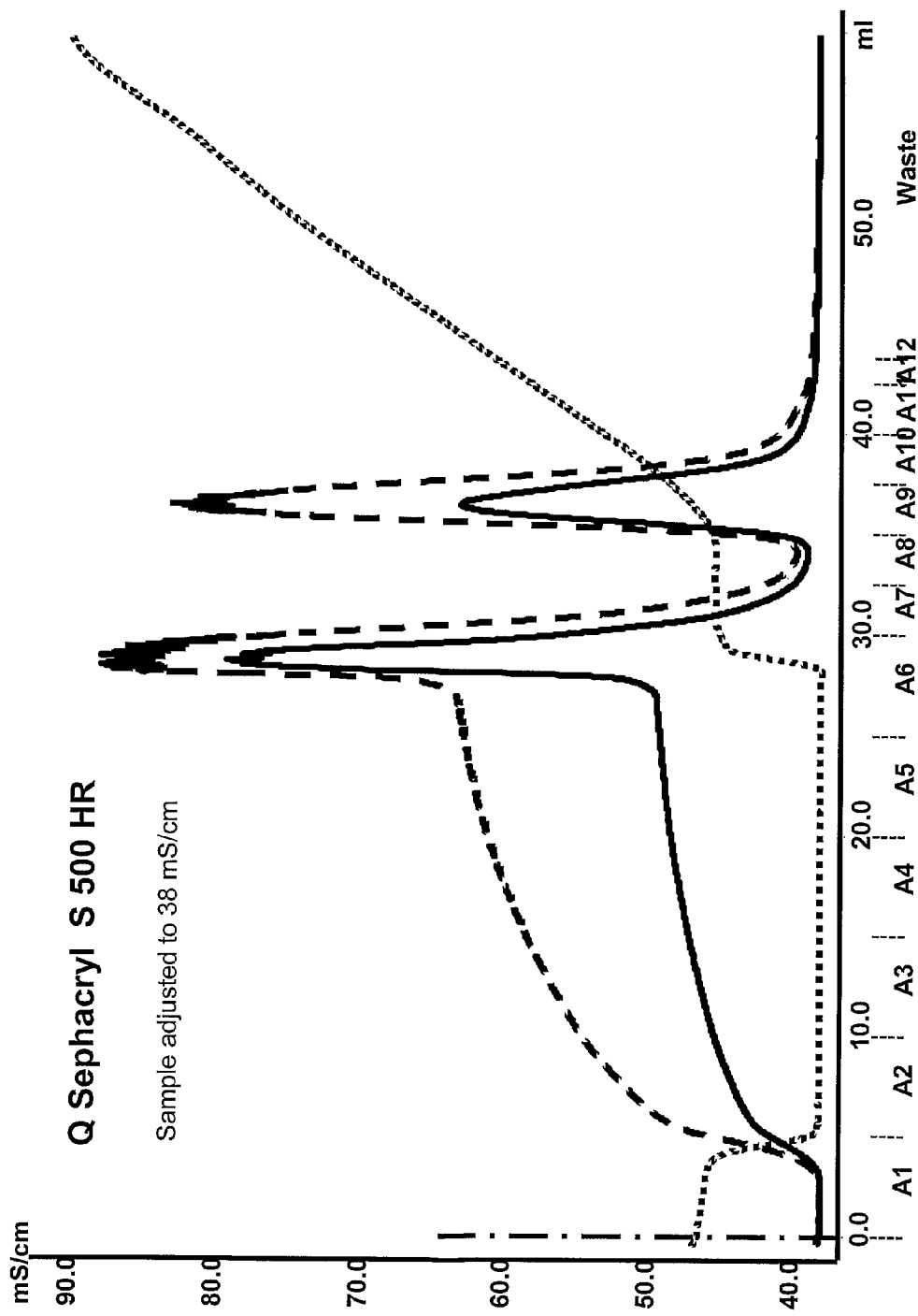
FIG. 2 shows a chromatogram illustrating isolation of plasmids as disclosed in the context of FIG. 1, using an adjusted conductivity.

FIG. 2 shows a chromatogram illustrating isolation of plasmids as disclosed in the context of FIG. 1, using a conductivity adjusted to 38 mS/cm.

Figure 3:
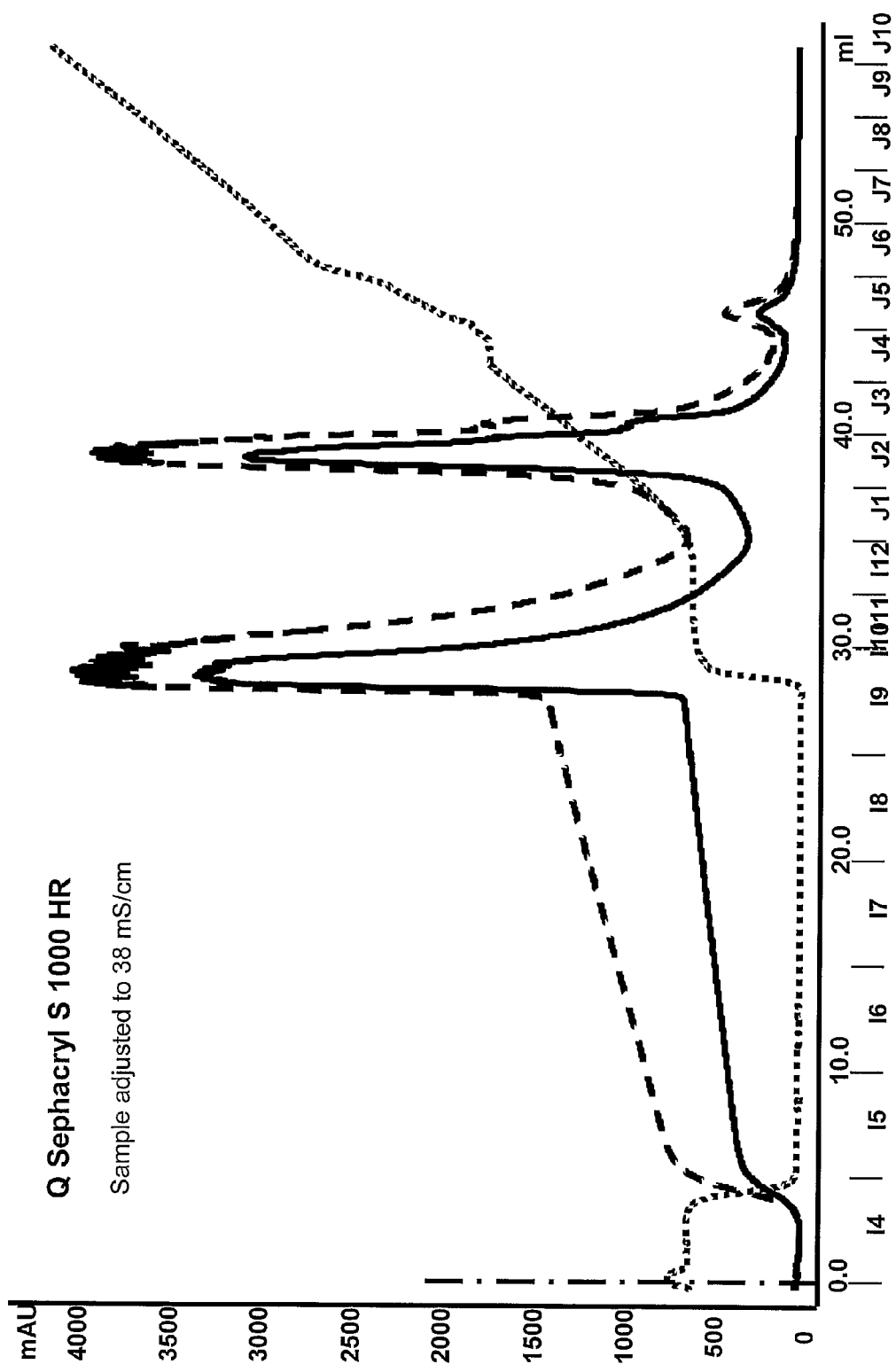
FIG. 3 shows a chromatogram illustrating isolation of plasmids from a cleared lysate according to the invention on a separation matrix equivalent to the one disclosed in the context of FIG. 1, except that it presents a higher DNA exclusion limit.

FIG. 3 shows a chromatogram illustrating isolation of plasmids according to the invention on a separation matrix equivalent to the one disclosed in the context of FIG. 1, except that it presents a DNA exclusion limit of 20,000 base pairs.

Figure 4:
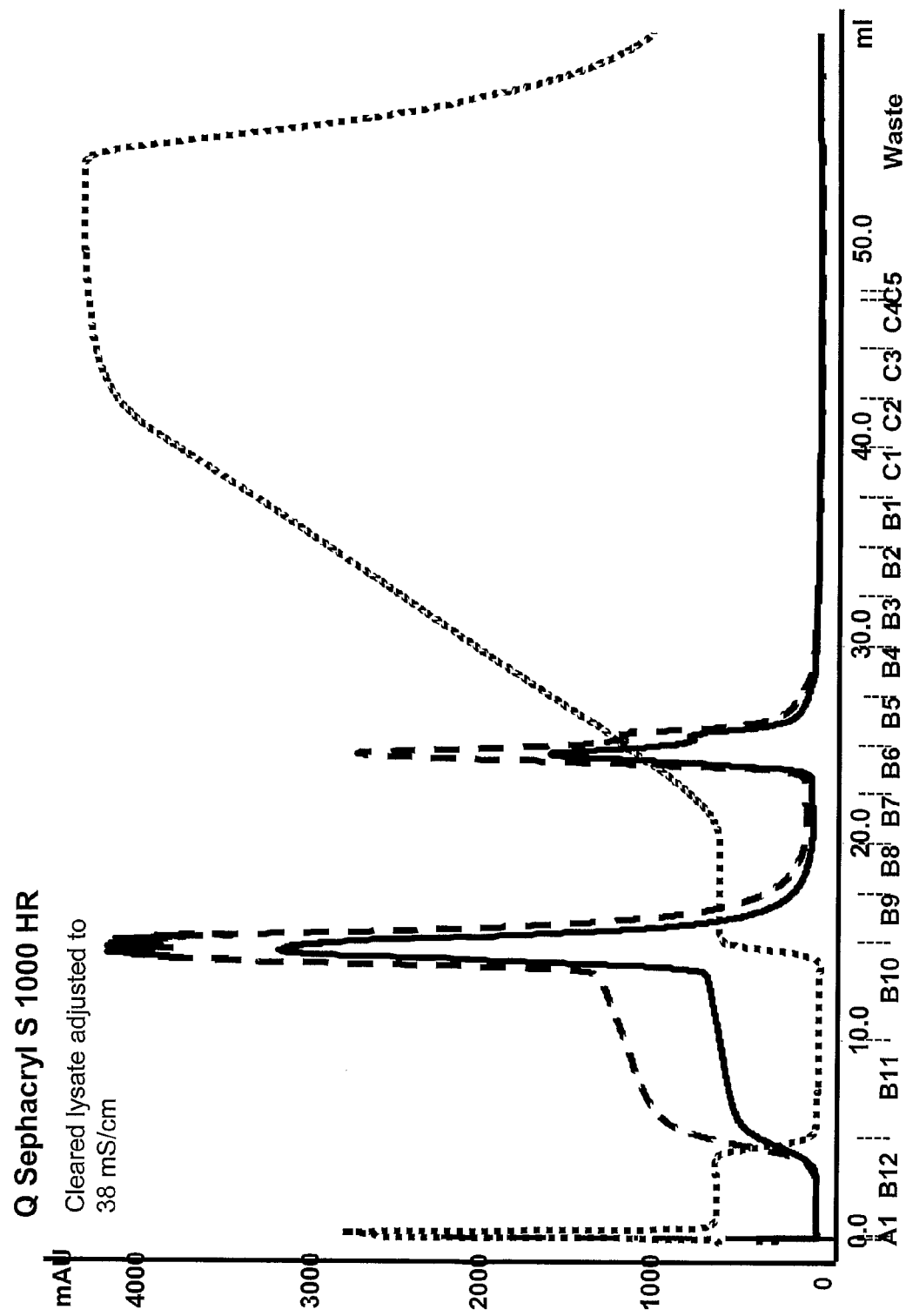
FIG. 4 shows a chromatogram illustrating isolation of plasmids as disclosed in the context of FIG. 3.

FIG. 4 shows a chromatogram illustrating isolation of plasmids on the same separation matrix as used in FIG. 3 from a cleared lysate.

Figure 5:
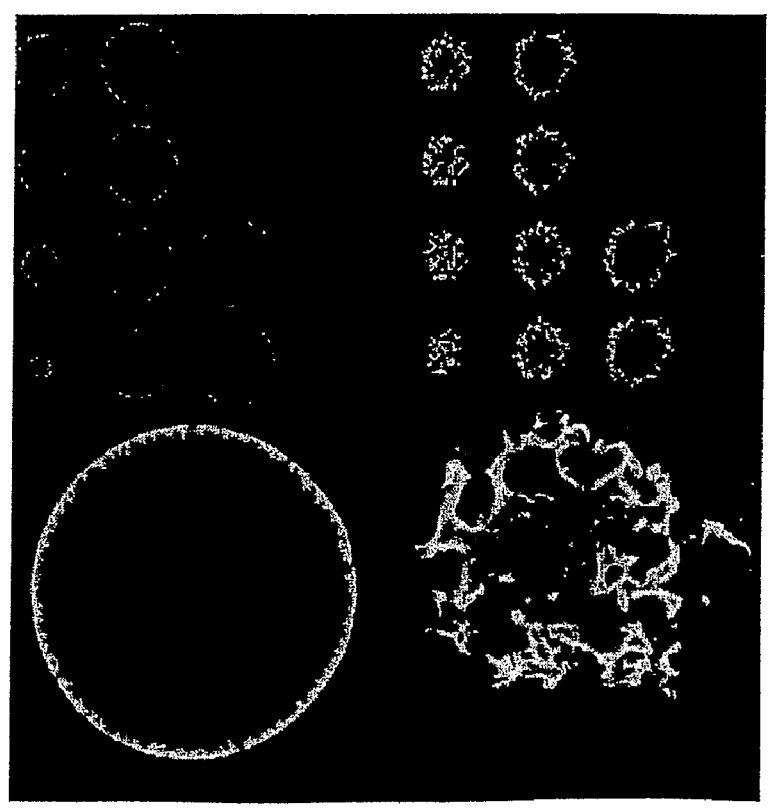
FIG. 5 is a confocal microscopy picture showing on the upper half one particle of a separation matrix, wherein the lighter surrounding area illustrates adsorbed plasmid according to the invention. The lower half is a comparison showing how plasmids enter the pores of a microcarrier used in cell culture.

FIG. 5 is a confocal microscopy picture showing on the upper half one particle of a separation matrix, wherein the lighter surrounding area illustrates adsorbed plasmid according to the invention. The pore size of the particle was 200 nm. The lower half is a comparison showing how plasmids enter the pores of a microcarrier used in cell culture (Cytodex™, Amersham Biosciences). Consequently, a conclusion would be that the capacity of a chromatography matrix for plasmids can be increased by decreasing the particle size, as surface is inversely correlated to its diameter.

EXAMPLES

Below, the present invention will be described by way of examples, which are provided for illustrative purposes only and accordingly are not to be construed as limiting the scope of the present invention as defined by the appended claims. All references given below and elsewhere in this application are hereby included herein by reference.

Example 1

Functionalisation of a Carrier Comprised of Allyl Dextran Cross-Linked with Bisacrylamide with Quaternary Ammonium (Q) Groups Sephacryl™ S-500 HR (Amersham Biosciences, Uppsala, Sweden) was drained by suction on a glass filter, and 200 g of the beads were added to a reaction vessel. 8.0 g sodium hydroxide and 0.2 g sodium borohydride were stirred with 40 ml distilled water to a clear solution and charged to the vessel. 400 ml glycidyltrimethylammonium chloride (GMAC) was pumped into the reaction vessel in 2 hours. The temperature was kept at 25° C. and the reaction continued during the night (18 hours). The product, herein denoted Q-Sephacryl™, was neutralised with 60% to acetic acid and washed with distilled water.

The amount of ion exchange ligands was determined by the following method. The volume of 1.0 ml gel was measured in a teflon cube. The sample was eluted with 0.5 M hydrochloric acid and washed with 1 mM hydrochloric acid. The gel was transferred to a titration cup with 10 ml of distilled water and 1 drop of concentrated nitric acid was added. Titration was finally done with 0.1 M silver nitrate. The result was 34 μmol $Cl^-$ per ml of gel.

Example 2

Functionalisation of Allyl Dextran Cross-Linked with Bisacrylamide with Amine Groups Example 2a Diethylamine Coupling 25 ml of the gel Sephacryl™ S500 HR (Amersham Biosciences, Uppsala, Sweden), which had been allylated with allylglycidyl ether (AGE) and NaOH according to standard methods to an allyl content of 140 μmol/ml, was vacuum drained and placed in a 600 ml beaker together with in 400 ml water. Bromine was added drop wise until a lasting yellow colour appeared in the suspension. The brominated gel was then washed on a glass filter funnel with more than 500 ml distilled water.

25 g of the above described brominated and vacuum drained gel was charged in a 100 ml round flask together with 4 g distilled water and 7 g diethylamine. The reaction was run at room temperature over night. The reaction was discontinued by washing the gel with about 2 bed volumes of water and then resuspension thereof in about 50 ml of water. The pH was adjusted to 5-6 by addition of a water:concentrated hydrochloric acid solution of 1:1. An additional wash with more than 500 ml of water was performed.

The ion exchange capacity (amount of ion exchanger) was determined to 63 μmol using standard methods.

Example 2b

Hydroxyethylamine Coupling 25 ml of the gel Sephacryl™ S500 (Amersham Biosciences, Uppsala, Sweden), which had been allylated as described in example 2a to an allyl content of 140 μmol/ml, was vacuum drained and placed in a 600 ml beaker together with in 400 ml water. Bromine was added dropwise until a lasting yellow colour appeared in the suspension. The brominated gel was then washed on a glass filter funnel with more than 500 ml distilled water.

25 g of the above described brominated and vacuum drained gel was charged in a 100 ml round flask together with 4 g distilled water and 5.85 g hydroxyethylamine. The reaction was run at room temperature over night. The reaction was discontinued by washing the gel with about 2 bed volumes of water and then resuspension thereof in about 50 ml of water. The pH was adjusted to 5-6 by addition of a water:concentrated hydrochloric acid solution of 1:1. An additional wash with more than 500 ml of water was performed.

The ion exchange capacity was determined to 54 μmol using standard methods.

Example 3

Chromatography

The sample was obtained starting from 35 g of bacterial cells (wet weight) containing 7 kb plasmid, and a cleared lysate was prepared according to a standard protocol. The resulting supernatant was concentrated/diafiltrated by ultrafiltration (UF) on hollow fiber module (300 kDa MWCO) to a final volume of 250 ml and a conductivity of 48 mS/cm, see FIG. 1. In a second run of experiments, the sample was been adjusted to a conductivity of 38 mS/cm by addition of water, see FIG. 2.

Both samples were applied in 10 respectively 25 ml volume quantities to PEEK columns (4.6/150 mm, 2.5 ml volume) packed with Q-Sephacryl™ S 500 HR or Q-Sephacryl™ S1000 HR, respectively. Q-Sephacryl™ S 500 HR was prepared as described in Example 1 above, while Q-Sephacryl™ S1000 HR was prepared in as disclosed in Example 1 bit starting from Sephacryl™ S1000 HR.

The flow rate was 0.4 ml/min (~130 cm/h), and the gradient after washing out of unbound sample was from 0.4M NaCl to 1M NaCl in 10 column volumes (CV). This was used for both sample preps:
Buffer A: 0.4 M NaCl, 100 mM Tris/Cl, 10 mM EDTA, pH 7.
Buffer B: 1M NaCl, 100 mM Tris/Cl, 10 mM EDTA, pH 7.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A method of isolating at least one plasmid from other component(s) of a liquid that includes RNA, comprising:
   (a) providing a separation matrix comprised of one or more porous carriers, which carrier(s) present anion exchange groups on external surfaces as well as pore surfaces and a pore size distribution that does not allow access of plasmids to pore surfaces;
   (b) contacting said matrix with the liquid to adsorb the plasmid(s) to ligands present on the external surfaces of the separation matrix and to adsorb the RNA to ligands present on the pore surfaces; and
   (c) contacting an eluent with the separation matrix to release the plasmid(s) and recovering plasmid(s) from a fraction of said eluent.

2. A method of isolating at least one plasmid from other component(s) of a liquid that includes RNA, comprising:
   (a) providing a separation matrix comprised of one or more porous carriers, which carrier(s) present anion exchange groups on external surfaces as well as pore surfaces and said pores have a DNA exclusion limit of at least about 270 base pairs;
   (b) contacting said matrix with the liquid to adsorb the plasmid(s) to ligands present on the external surfaces of the separation matrix and to adsorb the RNA to ligands present on the pore surfaces; and
   (c) contacting an eluent with the separation matrix to release the plasmid(s) and recovering plasmid(s) from a fraction of said eluent.

3. The method of claim 2, wherein the DNA exclusion limit of the separation matrix is at least about 1,000 base pairs.

4. The method of claim 1 or 2, wherein the separation matrix is in the form of essentially spherical particles having an average diameter of 30-50 μm.

5. The method of claim 1 or 2, wherein the plasmids are of a size that exceeds about 3,000 base pairs.

6. The method of claim 1 or 2, which is a large scale process wherein at least about 1 grams of plasmid is recovered.

7. The method of claim 1 or 2, wherein the plasmids recovered in step (c) are essentially free from RNA.

8. The method of claim 1 or 2, further comprising:
   (d) subjecting the plasmid-containing eluate obtained from step (c) to hydrophobic interaction chromatography (HIC).

9. The method of claim 1 or 2, wherein said anion-exchange groups are selected from the group consisting of quaternary amine (Q) groups and diethylamine groups.

* * * * *